United States Patent [19]

Sasao

[11] Patent Number: 5,049,826

[45] Date of Patent: Sep. 17, 1991

[54] LIQUID LEVEL SENSING APPARATUS FOR USE IN AUTOMATIC CHEMICAL ANALYSIS

[75] Inventor: Itsuro Sasao, Tochigi, Japan

[73] Assignee: Kabushiki Kaisha Toshiba, Kawasaki, Japan

[21] Appl. No.: 229,992

[22] Filed: Aug. 9, 1988

[30] Foreign Application Priority Data

Aug. 10, 1987 [JP] Japan ............................. 62-198103

[51] Int. Cl.$^5$ ........................ G01R 27/26; G05D 9/00
[52] U.S. Cl. ............................. 324/662; 73/864.24; 340/620; 422/106
[58] Field of Search ............... 324/661, 662, 664, 676, 324/689, 336, 71.1; 340/620, 603, 663; 73/864.24, 864.25, 304 C; 422/63, 67, 100, 106; 328/165, 167

[56] References Cited

U.S. PATENT DOCUMENTS

| | | | |
|---|---|---|---|
| 3,315,155 | 4/1967 | Colani | 324/336 X |
| 4,212,005 | 7/1980 | Hubert et al. | 340/603 |
| 4,585,997 | 4/1986 | Lin | 328/165 |
| 4,818,492 | 4/1989 | Shimizu | 73/864.24 X |
| 4,855,722 | 8/1989 | Mostyn et al. | 340/663 X |

*Primary Examiner*—Kenneth Wieder
*Assistant Examiner*—Jack B. Harvey
*Attorney, Agent, or Firm*—Oblon, Spivak, McClelland, Maier & Neustadt

[57] ABSTRACT

A liquid level sensing apparatus, including a bridge circuit sensitive to an element the impedance between a liquid sample and a pipette for providing a signal corresponding to the impedance, a phase detector for phase-detecting the output signal of the bridge circuit, a high-pass filter for differentiating the phase detection signal and a circuit for inhibiting the passage of a variation component of a signal from a band-pass filter and passing a liquid level signal component.

5 Claims, 3 Drawing Sheets

LIQUID LEVEL SENSING APPARATUS FOR USE IN AUTOMATIC CHEMICAL ANALYSIS

BACKGROUND OF THE INVENTION

1. Field of the Invention

This invention relates to a liquid level sensing apparatus for sensing the liquid level of liquid including serum in automatic chemical analysis.

2. Description of the Related Art

A well-known liquid level sensing apparatus used for an automatic chemical analyzer is disclosed in United States patent application Ser. No. 028,705 (filing data Mar. 20, 1987). This analyzer includes a bridge circuit, which generates a signal corresponding to a vertical displacement of a pipette for extracting a sample, a reagent, etc., when such movement is caused. The probe is connected as an element of the bridge circuit, and the bridge circuit generates an output signal corresponding to a change in the impedance between the probe and liquid level of sample accommodated in a sample container as the probe approaches the liquid level of the sample. When a CPU detects this signal, it provides a zero-setting signal corresponding to the input signal to an automatic phase controller. The automatic phase controller controls the phase of a reference signal from an oscillator according to the zero-setting signal to hold a phase difference of 90 degrees between the reference and input signals.

With this prior art liquid level sensing apparatus, the electrostatic capacitance between the pipette and liquid level is instable and varies due to vibrations of the pipette or the like stemming from the looseness of the mechanism of the analyzer for a predetermined period of time from the start of descent of the pipette. For this reason, the liquid level sensor detects the liquid level erroneously and produces an erroneous detection signal.

Further, the impedance between the pipette and sample surface is capacitive or inductive according to the kind of the sample. For example, if the sample is serum, the impedance is capacitive. With pure water, the impedance is inductive. With the variation of the detected impedance between capacitive and inductive impedances, negative and positive components corresponding to the capacitance and inductance, respectively, are generated as liquid level detection signals. When such opposite-phase detection signals are generated randomly, the liquid level is detected erroneously.

SUMMARY OF THE INVENTION

An object of the invention is to provide a liquid level sensing apparatus, which can prevent erroneous liquid level detection due to oscillation of the mechanism or other causes.

According to the invention, there is provided a liquid level sensing apparatus, in which the liquid level detection is inhibited for a predetermined period of time from the start of movement of a pipette for extracting the sample.

DETAILED DESCRIPTION OF THE PREFERRED EMBODIMENTS

Figure 1:
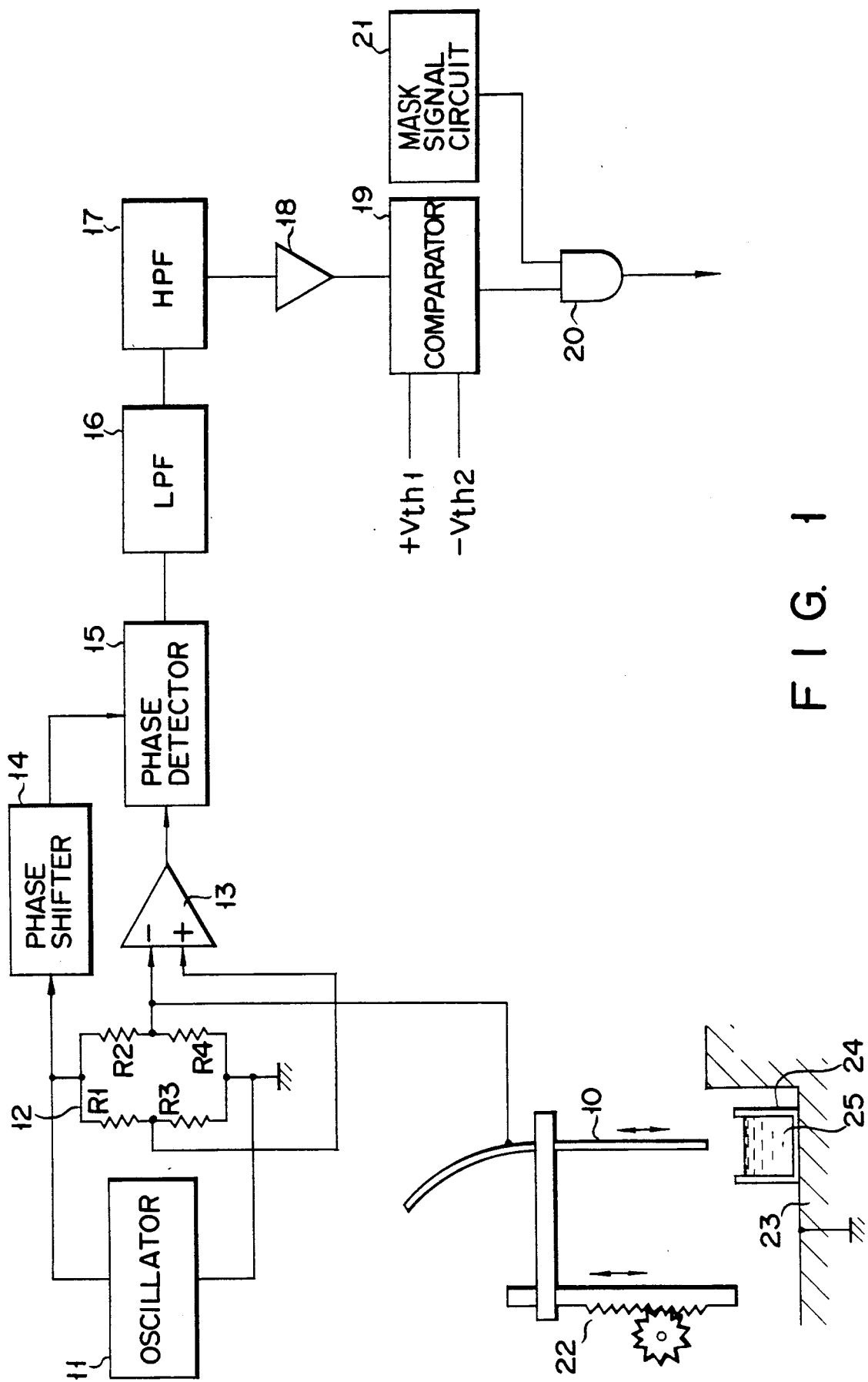
FIG. 1 is a block diagram showing an embodiment of the liquid level sensing apparatus according to the invention.

Referring to FIG. 1, oscillator 11 which generates a signal at 10 kHz or above is connected to bridge circuit 12. Bridge circuit 12 comprises four resistors R1 to R4 in bridge connection. One of its opposed nodes is connected to a non-inverted input terminal of operational amplifier 13, while the other node is connected to an inverted input terminal of operational amplifier 13 as well as to pipette 10. The output terminal of operational amplifier 13 is connected to phase detector 15, which is in turn connected to oscillator 11 through phase shifter 14.

Phase detector 15 phase-detects the output of operational amplifier 13 according to a signal from phase shifter 14. The output terminal of phase detector 15 is connected through low-pass filter 16 and high-pass filter 17 to amplifier 18. The output terminal of amplifier 18 is connected to comparator 19. Comparator 19 receives positive and negative threshold voltages Vth1 and Vth2 and compares the output signal of amplifier 18 to threshold voltages Vth1 and Vth2.

The output terminal of comparator 19 is connected to one input terminal of AND gate 20, the other input terminal of which is connected to the output terminal of mask signal circuit 21.

Probe or pipette 10 is held by lift mechanism 22. Back electrode 23 is disposed below pipette 10. Container 24 accommodating sample 25 is disposed on back electrode 23 such that it faces pipette 10.

Figure 2:
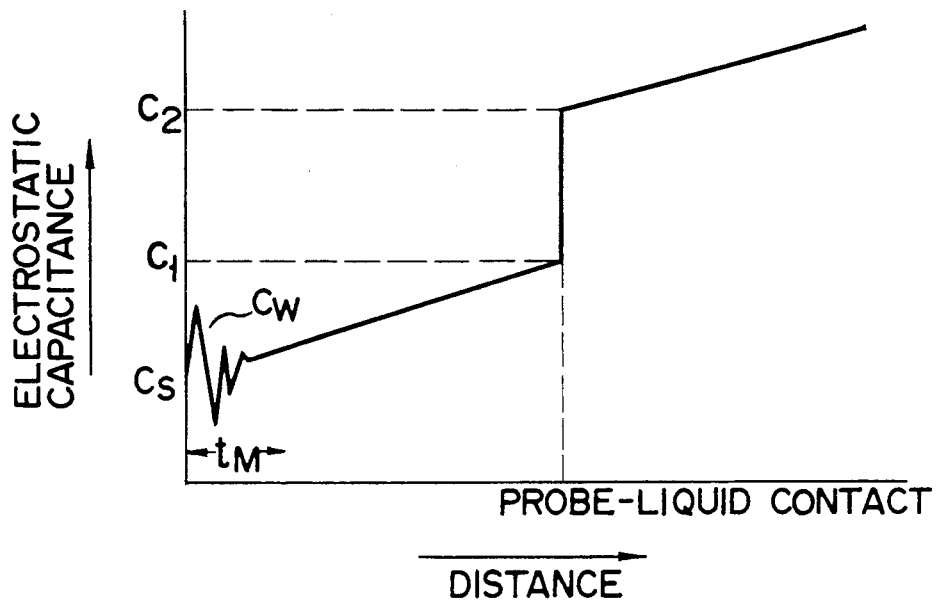
FIG. 2 is a graph showing the relation between the pipette position and electrostatic capacitance.

In the above liquid level sensing apparatus, when oscillator 11 is operated to supply an oscillation signal to bridge circuit 12 and lift mechanism 22 is driven according to a control command from, for instance, a CPU for controlling the analyzer to cause descent of pipette 10, the electrostatic capacitance between pipette 10 and back electrode 23 is increased as shown in FIG. 2 with decrease of the distance between pipette 10 and back electrode 23. In the graph of FIG. 2, electrostatic capacitance value Cs corresponds to the position of pipette 10 before the start of descent of pipette 10, and the electrostatic capacitance increases gradually from Cs to C1 with the descent of pipette 10. Electrostatic capacitance value C1 is obtained immediately before the end of pipette 10 reaches the surface of a sample, e.g., serum. When the end of pipette 10 reaches the surface of the serum, the electrostatic capacitance is suddenly increased from C1 to C2.

In the graph, variations Cw of the electrostatic capacitance that occur in an initial stage of the descent occur due to a swing or vibrations of pipette 10 caused due to defective dimensional accuracy of lift mechanism 22. The capacitance variation is of the order of several pF, and the period tM of variation is several 10 to several 100 milliseconds. If the variations are detected, an error is generated in the liquid level detection. For this reason, there is provided a circuit for masking the variation component, as will be described later.

Figure 3A:
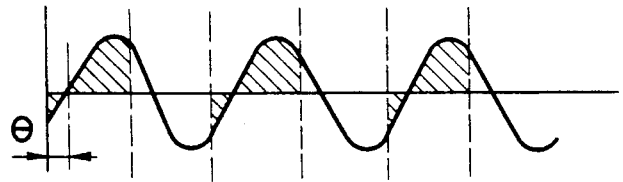
FIGS. 3A, 3B and 3C constitute a time chart showing signals input to and output from a phase detector.

The change in the electrostatic capacitance between pipette 10 and back electrode 23 is detected by bridge circuit 12. More specifically, the electrostatic capacitance provided between pipette 10 and back electrode 23 is connected in parallel to resistor R4 of bridge circuit 12, so that with a change in the electrostatic capacitance bridge circuit 12 provides a signal corresponding to the capacitance change to operational amplifier 13. Operational amplifier 13 amplifies this signal and provides a signal as shown in FIG. 3A to phase detector 15.

Figure 3B:
Figure 3C:
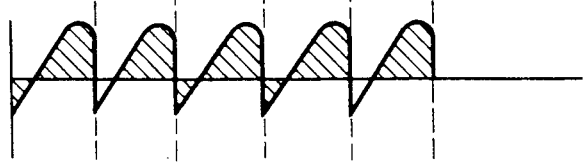

Phase detector 15 is receiving the output signal from phase shifter 14. Phase shifter 14 phase-shifts a signal provided from oscillator 11, and supplies the shifted signal to phase detector 15. Phase detector 15 converts the output signal of phase shifter 14 into a pulse signal as shown in FIG. 3. According to this pulse signal the output signal of operational amplifier 13 is phase-detected to produce a signal as shown in FIG. 3C.

The phase detection signal is supplied to low-pass filter 16. Low-pass filter 16 supplies the low-frequency component of the phase detection signal to high-pass filter 17. High-pass filter 17 differentiates the output signal of low-pass filter 16. Thus, a gently changing component of the output signal of low-pass filter 16 is converted into a flat component, while a sharply changing component of the output signal is passed through filter 17 directly. With the provision of this high-pass filter a signal corresponding to a change in the capacitance generated at the time of the start of fall of pipette 10 is suppressed and not detected as any detection signal.

Figure 4:
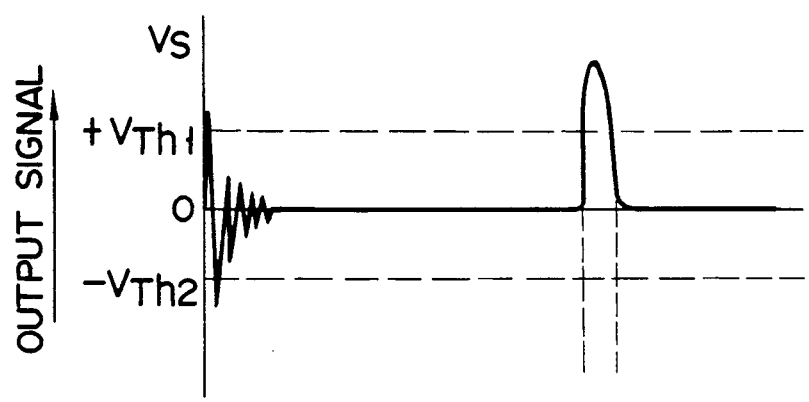
FIG. 4 is a graph showing an output signal of an amplifier shown in FIG. 1.

The output signal of high-pass filter 17 is amplified by amplifier 18 to be supplied as signal Vs having a waveform as shown in FIG. 4 to comparator 19. Comparator 19 compares signal Vs to threshold values $+Vth1$ or $-Vth2$ If signal Vs is beyond the range between threshold values $+Vth1$ and $-Vth2$, comparator 19 detects detection signal. More specifically, signal Vs which is below the threshold level is ignored as error signal.

Now, threshold values $+Vth1$ and $-Vth2$ will be described.

In case where sample 25 is a serum or a reagent for reaction thereof or like liquid having high dielectric constant and containing ions, the entire liquid is held at the same potential, so that the impedance change substantially coincides with a capacitive component change. For this reason, the phase detection output signal greatly contains the positive component. In this case, signal Vs is compared to threshold value $+Vth1$. In case where sample 25 is pure water or like liquid having low dielectric constant and substantially showing no electric conductivity, the entire liquid is not held at the same potential, so that the impedance change substantially coincides with an inductive component change. Thus, signal Vs greatly contains a negative component. In this case, signal Vs is compared to threshold value $-Vth2$. The sample thus can be reliably detected irrespective of whether it is inductive or capacitive.

Figure 5:
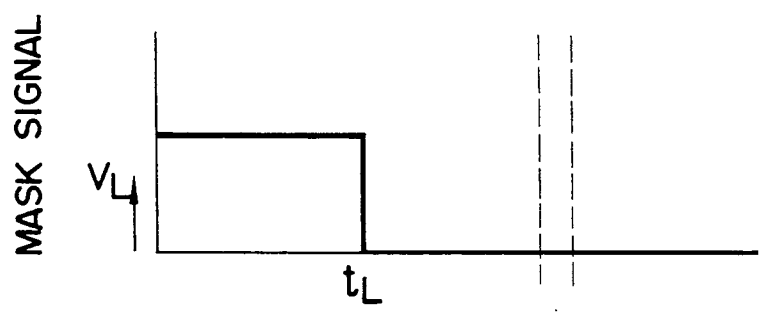
FIG. 5 is a graph showing a mask signal.
Figure 6:
FIG. 6 is a graph showing a liquid level sensing apparatus.

The output signal of comparator 19 is supplied to one input terminal of AND gate 20, to the other input terminal of which is supplied a mask signal as shown in FIG. 5 from mask signal circuit 21. Mask signal, as noted before, has a constant-time pulse duration tM which can sufficiently cover the period tM (several 10 to several 100 milliseconds), of initial stage of descent of pipette 10, during which the electrostatic capacitance is stable and varies. With this mask signal supplied to AND gate 20, the instable signal component is never detected as liquid level detection signal as shown in FIG. 6, and a true liquid level detection signal is provided through AND gate 20. The mask signal circuit comprises a mono-stable multivibrator which provides a mask signal having a predetermined pulse duration in response to a detection signal detecting the upper dead center of the pipette.

In the above embodiment the phase detection signal is filtered through the low-pass and high-pass filters, but it is possible to filter the signal through a band-pass filter.

What is claimed is:

1. A liquid level sensing apparatus for detecting the reaching of the surface of a liquid sample by pipette means moved toward said liquid sample for extraction thereof, comprising:

impedance detection means having bridge circuit means connected to said pipette means and liquid sample, including as an impedance element the impedance between said pipette mans and liquid sample and providing a signal corresponding to the impedance;

converting means including phase detection means for phase-detecting said signal from said impedance detection means and outputting a phase-detection signal, which contains an impedance variation component generated in an initial stage of movement of said pipette means and a liquid level detection signal component corresponding to the detection of the liquid level of said liquid sample; and liquid level signal detection means for removing said impedance variation component from said phase-detection signal from said converting means and detecting the liquid level detection signal component.

2. The liquid level sensing apparatus according to claim 1, wherein sad converting means includes high-pass filter means for differentiating the phase-detection signal of said phase detection means.

3. The liquid level sensing apparatus according to claim 1, wherein said liquid level signal detection means comprises means for inhibiting the passage of the detection signal from said converting means for a predetermined period of time from the start of movement of said pipette means.

4. The liquid level detection means according to claim 3, wherein said liquid level signal detection means includes mask signal means for producing a mask signal having a pulse width corresponding to a predetermined period of time from said start of movement and gate means for gating the detection signal from said converting means according to the mask signal from said mask signal means.

5. The liquid level detection means according to claim 1, wherein said liquid level signal detection means includes comparator means for comparing the detection signal from said converting means to a first threshold value and a second threshold value of the opposite polarity to said first threshold value and providing said detection signal as a liquid level detection signal when the value of said detection signal is beyond a range between said first and second threshold values.

* * * * *